United States Patent
Kaoukhov et al.

(10) Patent No.: US 8,563,524 B2
(45) Date of Patent: Oct. 22, 2013

(54) COMPOSITIONS COMPRISING AVERMECTIN/AZELAIC ACID COMPOUNDS USEFUL FOR TREATING E.G., ROSACEA

(75) Inventors: Alexandre Kaoukhov, Luan les Pins (FR); Colette Pernin, Nice (FR)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 13/410,234

(22) Filed: Mar. 1, 2012

(65) Prior Publication Data

US 2013/0064780 A1 Mar. 14, 2013

Related U.S. Application Data

(63) Continuation of application No. 12/830,576, filed on Jul. 6, 2010, now abandoned, which is a continuation of application No. 11/898,911, filed on Sep. 17, 2007, now abandoned, which is a continuation of application No. PCT/FR2006/000570, filed on Mar. 15, 2006.

(30) Foreign Application Priority Data

Mar. 17, 2005 (FR) ..................................... 05 02645

(51) Int. Cl.
*A61K 31/70* (2006.01)
(52) U.S. Cl.
USPC ............................................................ 514/30
(58) Field of Classification Search
USPC ............................................................ 514/30
See application file for complete search history.

(56) References Cited

U.S. PATENT DOCUMENTS

| 5,952,372 A | 9/1999 | McDaniel |
| 2006/0100165 A1 | 5/2006 | Manetta et al. |

FOREIGN PATENT DOCUMENTS

| FR | 2854074 A1 | 10/2004 |
| WO | WO 2004/022046 A1 | 3/2004 |

OTHER PUBLICATIONS

Thiboutot et al., "Efficacy and Safety of Azelaic Acid (15%) Gel as a New Treatment of Papulopustural Rosacea." *J. Am. Acad. Dermatol.* 2003, vol. 48, pp. 835-845, C.V. Mosby, St. Louis. MO.
International Search Report corresponding to PCT/FR2006/00570 issued Jun. 19, 2006.
Forton et al., "Demodicosis and rosacea: Epidemiology and significance in daily dermatologic practice", J. Am. Acad. Dermatol., Jan. 2005, pp. 74-87, vol. 52, No. 1, C.V. Mosby, St. Louis, MO.
Loo et al., "Invermetin cream in rosacea: comparison metronidazole gel", British Journal of Dermatology, 2004, p. 21, vol. 151, Suppl. 68, XP009056313, GB.
Thiboutot et al., "Efficacy and Safety of Azelaic Acid (15%) Gel as a New Treatment of Papulopustural Rosacea." *J. Am. Acad. Dermatol.* 2003, vol. 48, pp. 835-845, C.V. Mosby, St. Louis. MO.

*Primary Examiner* — Elli Peselev
(74) *Attorney, Agent, or Firm* — Dentons US LLP

(57) ABSTRACT

Pharmaceutical/dermatological compositions useful for the prevention/treatment of disorders of the skin, especially rosacea, contain thus effective amounts of at least one avermectin compound, e.g., ivermectin, and at least one azelaic acid compound or salt or derivative thereof, formulated into a physiologically acceptable medium therefor.

24 Claims, No Drawings

COMPOSITIONS COMPRISING AVERMECTIN/AZELAIC ACID COMPOUNDS USEFUL FOR TREATING E.G., ROSACEA

CROSS-REFERENCE TO EARLIER APPLICATIONS

This application to a continuation of application Ser. No. 12/830,576, filed Jul. 6, 2010, now abandoned, which is a continuation of application Ser. No. 11/898,911, filed Sep. 17, 2007, now abandoned, which is a continuation of PCT/FR 2006/000570, filed Mar. 15, 2006 and designating the United States (published in the French language on Sep. 21, 2006 as WO 2006/097628 A1; the title and abstract were also published in English), which claims priority under 35 U.S.C §119 of FR05/02645, filed Mar. 17, 2005, each hereby expressly incorporated by reference in its entirety and each assigned to the assignee hereof.

BACKGROUND OF THE INVENTION

1. Technical Field of the Invention

The present invention relates to pharmaceutical compositions, and especially dermatological compositions, for treating skin conditions, and especially for treating rosacea (formerly known as acne rosacea). In particular, this invention relates to pharmaceutical compositions, especially dermatological compositions, comprising, formulated into a physiologically acceptable medium, at least one compound of the avermectin family and azelaic acid.

The present invention also relates to pharmaceutical compositions, especially dermatological compositions, comprising, formulated into a physiologically acceptable medium, at least ivermectin and azelaic acid. The invention also relates to the administration of such compositions as medicaments for treating skin conditions, disorders or afflictions, in particular rosacea.

2. Description of Background and/or Related and/or Prior Art

Rosacea is a chronic inflammatory dermatitis that mainly affects the median part of the face and the eyelids of certain adults. It is characterized by telangiectatic erythema, dryness of the skin, papules and pustules.

Conventionally, rosacea develops in adults from the ages of 30 to 50; it more frequently affects women, although the condition is generally more severe in men.

Despite its former name, acne rosacea is not a condition of the pilosebaceous follicles like juvenile acne, but a primitively vascular condition whose inflammatory stage lacks the cysts and comedones characteristic of common acne.

The aetiology of rosacea is still poorly understood, although many theories have been advanced. The most common hypothesis is based on the characteristic presence of the parasite *Demodex folliculorum* in the case of patients suffering from rosacea. This organism is absent in common acne. Other factors have been described as possibly contributing towards the development of rosacea, such as hormonal factors and especially endocrine factors, climatic and immunological factors, and bacterial factors via the presence of *Helicobacter pylori*, a bacterium associated with gastrointestinal disorders.

Rosacea develops in four stages over several years, in spasms aggravated by variations in temperature, alcohol, spices, exposure to sunlight and emotions. The various stages of the disease are the following:

Stage 1: stage of erythema episodes. The patients have erythrosis spasms due to the sudden dilation of the arterioles of the face, which then take on a congestive, red appearance. These spasms are caused by the emotions, meals and temperature changes.

Stage 2: stage of couperosis, i.e., of permanent erythema with telangiectasia. Certain patients also have oedema on the cheeks and the forehead.

Stage 3: inflammatory stage with appearance of inflammatory papules and pustules, but without affecting the sebaceous follicles and thus with absence of cysts and comedones.

Stage 4: rhinophyma stage. This late phase essentially affects men. The patients exhibit a bumpy, voluminous red nose with sebaceous hyperplasia and fibrous reordering of the connective tissue.

Conventionally, rosacea is treated orally or topically with antibiotics such as tetracyclines, erythromycin, clindamycin or metronidazole, but also with vitamin A, salicylic acid, anti-fungal agents, steroids, anti-infectious agents such as benzoyl peroxide, with isotretinoin or with azelaic acid.

Azelaic acid (or 1,7-heptanedicarboxylic acid) is known in the prior art for its anti-acne and keratolytic properties. Azelaic acid shows anti-bacterial activity on *P. acnes* and *S. epidermidis*. It inhibits keratinocyte proliferation, reduces the level of free fatty acid in sebaceous secretions and also has anti-inflammatory activity.

WO 2004/022 046 describes a method for treating rosacea via topical application of a composition based on azelaic acid and metronidazole.

U.S. Pat. No. 5,952,372 also describes a method for treating rosacea using ivermectin orally or topically in order to reduce and eliminate the parasite *Demodex folliculorum* present on the skin of patients.

Ivermectin belongs to the avermectin family, a group of macrocyclic lactones produced by the bacterium *Streptomyces avermitilis* (Reynolds JEF (Ed) (1993) Martindale. The Extra Pharmacopoeia. 29th Edition. Pharmaceutical Press, London). The avermectins especially include ivermectin, invermectin, avermectin, abamectin, doramectin, eprinomectin and selamectin.

Ivermectin is known in the prior art for its anti-parasitic and anthelmintic properties. The anti-parasitic activity is thought to be due to the opening of a chlorine channel in the membrane of the neurons of the parasite under the effect of an increased release of the neuromediator GABA (gamma-aminobutyric acid), inducing neuromuscular paralysis that may lead to the death of certain parasites. Ivermectin also interacts with other chlorine channels, especially those dependent on the neuromediator GABA (gamma-aminobutyric acid). It is already described in man in the treatment of onchocercosis caused by *Onchocerca volvulus*, gastrointestinal strongyloidosis (anguillulosis) (product Stromectol®), human scabies (Meinking T. L. et al., *N. Engl. J. Med.* 1995, Jul. 6; 333 (1): 26-30 The treatment of scabies with ivermectin) and also in the treatment of diagnosed or suspected microfilaraemia in the case of individuals suffering from lymphatic filariasis caused by *Wuchereria bancrofti*.

U.S. Pat. No. 6,133,310 describes the administration of ivermectin in the treatment of rosacea in order to reduce and eliminate the parasite *Demodex folliculorum* present on the skin of patients.

However, these treatments have drawbacks such as irritation and intolerance phenomena, especially when they are administered for a prolonged period. Furthermore, these treatments are only suppressive and not curative, acting especially on the pustulous spasms occurring during the inflammatory stage.

Considering the chronic nature of rosacea, the ideal treatment requires prolonged use, in a safe and effective manner.

Taking the foregoing into account, there is thus a need for a composition that shows improved efficacy in the treatment of rosacea and that does not exhibit the side effects described in the prior art. There is especially a need to formulate a composition that imparts greater tolerance to the active principles, while at the same time reducing their side effects.

SUMMARY OF THE INVENTION

Accordingly, the present invention features compositions comprising a combination of at least one compound of the avermectin family and azelaic acid, which are useful for treating rosacea.

This invention thus features pharmaceutical compositions, especially dermatological compositions, comprising, formulated into a physiologically acceptable medium, at least one compound of the avermectin family and azelaic acid.

The term "physiologically acceptable medium" means any medium that is compatible with the skin, mucous membranes and/or the integuments.

DETAILED DESCRIPTION OF BEST MODE AND SPECIFIC/PREFERRED EMBODIMENTS OF THE INVENTION

The azelaic acid according to the invention may be formulated in unmodified form, or, alternatively, in the form of a salt with a pharmaceutically acceptable base, or else in the form of a derivative. The term "derivatives" means compounds that differ from azelaic acid by substitution, addition or removal of one or more chemical groups and that have substantially the same activity.

The present invention thus features pharmaceutical compositions, especially dermatological compositions, comprising, formulated into a physiologically acceptable medium, at least one compound of the avermectin family, and at least one compound selected from among azelaic acid and salts and derivatives thereof.

This invention preferentially features pharmaceutical compositions, especially dermatological compositions, comprising, formulated into a physiologically acceptable medium, at least ivermectin and azelaic acid.

This invention also features the administration of such compositions, whether a regime or regimen, as medicaments for preventing and/or treating a skin condition, disorder or affliction.

The present invention and the advantages resulting therefrom will be understood more clearly from the description of the non-limiting embodiments that follow.

The compounds of the avermectin family that may be formulated according to the present invention especially include invermectin, ivermectin, avermectin, abamectin, doramectin, eprinomectin and selamectin. The compound of the avermectin family is preferentially ivermectin.

In the compositions according to the invention, the said compound of the avermectin family is present in concentrations of from 0.001% to 10% by weight and preferably from 0.01% to 5% by weight relative to the total weight of the composition.

In the compositions according to the invention, the azelaic acid and the salts and/or derivatives thereof are present in concentrations of from 0.01% to 40% by weight and preferably from 1% to 20% by weight relative to the total weight of the composition.

Throughout the present text, unless otherwise specified, it is understood that when concentration ranges are given, they include the upper and lower limits of the said range.

Advantageously, the compositions of the invention comprise, besides at least one compound of the avermectin family and azelaic acid, at least one other therapeutic active agent suitable for increasing the efficacy of the treatment. Non-limiting examples of such agents include antibiotics, anti-bacterial agents (for instance metronidazole), anti-viral agents, anti-parasitic agents, anti-fungal agents, anaesthetics, analgesics, anti-allergic agents, retinoids, free-radical scavengers, anti-pruritic agents, keratolytic agents, anti-seborrhoeic agents, anti-histamines, sulfides, and immunosuppressant or anti-proliferative products, or a mixture thereof.

The compositions according to the invention may also comprise any adjuvant usually employed in dermatology that is compatible with the said compound of the avermectin family and azelaic acid. Especially representative are chelating agents, antioxidants, sunscreens, preservatives, fillers, electrolytes, humectants, dyes, common mineral or organic acids or bases, fragrances, essential oils, cosmetic active agents, moisturizers, vitamins, essential fatty acids, sphingolipids, self-tanning compounds, calmatives and skin-protecting agents, pro-penetrating agents and gelling agents, or a mixture thereof. These additives, and the concentrations thereof, should be such that they do not adversely affect the advantageous properties of the mixtures according to the invention. These additives may be present in the composition in a proportion of from 0% to 20% by weight and preferably from 1% to 10% by weight relative to the total weight of the composition.

Examples of preservatives include benzalkonium chloride, phenoxyethanol, benzyl alcohol, diazolidinylurea and parabens, or mixtures thereof.

Humectants that are exemplary, in particular, include glycerol and sorbitol.

Examples of chelating agents include ethylenediaminetetraacetic acid (EDTA) and also derivatives or salts thereof, dihydroxyethylglycine, citric acid and tartaric acid, or mixtures thereof.

Pro-penetrating agents that are exemplary, in particular, include propylene glycol, dipropylene glycol, propylene glycol dipelargonate, lauryl glycol and ethoxydiglycol.

The compositions according to the invention are useful for treating and/or preventing rosacea.

According to a first embodiment of the invention, the administration of the composition is as a medicament for treating and/or preventing a skin condition and preferably for treating and/or preventing rosacea, common acne and/or seborrhoeic dermatitis and particularly preferably for treating rosacea.

The present invention also features the use of at least one compound of the avermectin family for the formulation of pharmaceutical compositions, especially dermatological compositions, for preventing and/or treating a skin condition, the compound of the avermectin family being combined in the said composition with azelaic acid. In this embodiment, the composition is as defined above.

The compositions according to the invention are preferably for topical application.

The compositions according to the invention are pharmaceutical compositions, and especially dermatological compositions, which may be in any galenical form conventionally used for topical application and especially in the form of aqueous gels, and aqueous or aqueous-alcoholic solutions. By addition of a fatty or oily phase, same may also be in the form of dispersions of the lotion or serum type, emulsions of liquid or semi-liquid consistency of the milk type obtained by dispersing a fatty phase in an aqueous phase (O/W) or conversely (W/O), or suspensions or emulsions of soft, semi-liquid or solid consistency of the cream, gel or ointment type, or, alternatively, multiple emulsions (W/O/W or O/W/O), microemulsions, microcapsules, microparticles or vesicular dispersions of ionic and/or nonionic type, or wax/aqueous phase dispersions. These compositions are prepared according to the usual methods.

When the composition is in emulsion form, the proportion of the oily phase of the emulsion may range, for example, from 5% to 80% by weight and preferably from 5% to 50% by weight relative to the total weight of the composition. The oils, emulsifiers and co-emulsifiers used in the composition in emulsion form are selected from among those conventionally used in dermatology. The emulsifier and the co-emulsifier are generally present in the composition in a proportion ranging from 0.3% to 30% by weight and preferably from 0.5% to 20% by weight relative to the total weight of the composition. The emulsion may also contain lipid vesicles.

As fatty substances according to the invention, it is possible to use oils and especially mineral oils (liquid petroleum jelly), oils of plant origin (avocado oil or soybean oil), oils of animal origin (lanolin), synthetic oils (perhydrosqualene), silicone oils (cyclomethicone) and fluoro oils (perfluoropolyethers). Fatty alcohols such as cetyl alcohol, fatty acids, waxes and gums, in particular silicone gums, may also be used as fatty substances.

As emulsifiers and co-emulsifiers according to the invention, examples thereof include fatty acid esters of polyethylene glycol such as PEG-100 stearate, PEG-50 stearate and PEG-40 stearate; fatty acid esters of polyols such as glyceryl stearate, sorbitan tristearate and the oxyethylenated sorbitan stearates available under the trademark Tween 20 or Tween 60, for example; and mixtures thereof.

Non-limiting examples of gelling agents include the polyacrylamide family such as the sodium acryloyldimethyltaurate copolymer/isohexadecane/polysorbate 80 mixture marketed under the trademark Simulgel™ 600 by SEPPIC, the polyacrylamide/C13-14 isoparaffin/Laureth-7 mixture, for instance the product marketed under the trademark Sepigel 305™ by SEPPIC, the family of acrylic polymers coupled to hydrophobic chains, such as the PEG-150/decyl/SMDI copolymer marketed under the trademark Aculyn 44™ (polycondensate comprising at least, as components, a polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%)), and the family of modified starches such as the modified potato starch marketed under the trademark Structure Solanace™, or mixtures thereof.

The preferred gelling agents are derived from the polyacrylamide family, such as Simulgel 600™ or Sepigel 305™, or mixtures thereof.

The gelling agent as described above may be used in a concentration ranging from 0.1% to 15% to preferably from 0.5% to 5%.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pharmaceutical/dermatological topically applicable composition useful for the treatment of rosacea in the absence of irritation and intolerance, comprising anti-rosacea effective amounts of ivermectin and azelaic acid or salt thereof, and a gelling agent selected from the group consisting of acrylamide/sodium acryloyldimethyltaurate copolymer/isohexane/polysorbate 80 gelling agent and polyacrylamide/C13-14 isoparaffin/laureth-7 gelling agent, formulated into a topically applicable, physiologically acceptable medium therefor, wherein ivermectin and azelaic acid or salt thereof are the only active anti-rosacea agents in the composition, said composition being formulated as a gel or an emulsion.

2. The pharmaceutical/dermatological composition as defined by claim 1, said ivermectin comprising from 0.001% to 10% by weight thereof.

3. The pharmaceutical/dermatological composition as defined by claim 2, said azelaic acid or salt thereof comprising from 0.01% to 40% by weight thereof.

4. The pharmaceutical/dermatological composition as defined by claim 1, formulated as a gel.

5. The pharmaceutical/dermatological composition as defined by claim 1, formulated as an emulsion.

6. The pharmaceutical/dermatological composition as defined by claim 1, further comprising at least one additive selected from the group consisting of chelating agents, antioxidants, sunscreens, preservatives, fillers, electrolytes, humectants, dyes, mineral acids, organic acids, mineral bases, organic bases, fragrances, essential oils, moisturizers, vitamins, essential fatty acids, sphingolipids, self-tanning compounds, calmatives, skin-protecting agents, pro-penetrating agents, and mixtures thereof.

7. A method for the treatment of rosacea, comprising topically administering to an individual in need of such treatment, a pharmaceutical/dermatological topically applicable composition comprising anti-rosacea effective amounts of ivermectin and azelaic acid or salt thereof, and a gelling agent selected from the group consisting of acrylamide/sodium acryloyldimethyltaurate copolymer/isohexane/polysorbate 80 gelling agent and polyacrylamide/C13-14 isoparaffin/laureth-7 gelling agent, formulated into a topically applicable, physiologically acceptable medium therefor, wherein ivermectin and azelaic acid or salt thereof are the only active anti-rosacea agents in the composition, said composition being formulated as a gel or an emulsion.

8. The pharmaceutical/dermatological composition as defined by claim 1, said ivermectin comprising from 0.01% to 5% by weight thereof and said azelaic acid or salt thereof comprising from 1% to 20% by weight thereof.

9. The pharmaceutical/dermatological composition as defined by claim 5, wherein the emulsion is a cream.

10. The pharmaceutical/dermatological composition as defined by claim 8, formulated as an emulsion.

11. The pharmaceutical/dermatological composition as defined by claim 10, wherein the emulsion is a cream.

12. The pharmaceutical/dermatological composition as defined by claim 8, formulated as a gel.

13. The pharmaceutical/dermatological composition as defined by claim 6, said ivermectin comprising from 0.01% to 5% by weight thereof and said azelaic acid or salt thereof comprising from 1% to 20% by weight thereof.

14. The pharmaceutical/dermatological composition as defined by claim 9, said ivermectin comprising from 0.01% to 5% by weight thereof and said azelaic acid or salt thereof comprising from 1% to 20% by weight thereof.

15. The method as defined by claim 7, said ivermectin comprising from 0.01% to 5% by weight of the composition and said azelaic acid or salt thereof comprising from 1% to 20% by weight of the composition.

16. The method as defined by claim 15, wherein the composition is formulated as an emulsion.

17. The method as defined by claim 16, wherein the emulsion is a cream.

18. The method as defined by claim 15, wherein the composition is formulated as a gel.

19. A pharmaceutical/dermatological topically applicable composition useful for the treatment of rosacea in the absence of irritation and intolerance, consisting of anti-rosacea effective amounts of ivermectin and azelaic acid or salt thereof, and a gelling agent selected from the group consisting of acrylamide/sodium acryloyldimethyltaurate copolymer/isohexane/polysorbate 80 gelling agent and polyacrylamide/C13-14 isoparaffin/laureth-7 gelling agent, formulated into a topically applicable, physiologically acceptable medium therefor, said medium consisting of: (a) at least one member selected from the group consisting of water, alcohols, oils, fatty substances and waxes, and (b) at least one additive selected from the group consisting of chelating agents, antioxidants, sunscreens, preservatives, fillers, electrolytes, humectants, dyes, mineral acids, mineral bases, organic acids, organic bases, fragrances, essential oils, moisturizers, vitamins, essential fatty acids, sphingolipids, self-tanning compounds, calmatives, skin-protecting agents, pro-penetrating agents, emulsifiers, co-emulsifiers, and mixtures thereof, said composition being formulated as a gel or an emulsion.

20. The pharmaceutical composition as defined by claim 19, said ivermectin being from 0.01% to 5% by weight thereof and said azelaic acid or salt thereof being from 1% to 20% by weight thereof.

21. The pharmaceutical/dermatological composition as defined by claim 20, formulated as an emulsion.

22. The pharmaceutical/dermatological composition as defined by claim 21, wherein the emulsion is a cream.

23. The pharmaceutical/dermatological composition as defined by claim 20, formulated as a gel.

24. A method for the treatment of rosacea, comprising topically administering to an individual in need of such treatment, an anti-rosacea effective amount of a composition as defined by claim 19.

* * * * *